United States Patent [19]

Cooper

[11] 3,946,003

[45] Mar. 23, 1976

[54] HYDROXY SUBSTITUTED PHENYLGLYCYLAMIDO-3-HETEROCYCLIC THIOMETHYL CEPHALOSPORINS

[75] Inventor: Robin D. G. Cooper, Indianapolis, Ind.

[73] Assignee: Eli Lilly and Company, Indianapolis, Ind.

[22] Filed: Aug. 20, 1974

[21] Appl. No.: 498,886

[52] U.S. Cl. .............................. 260/243 C; 424/246
[51] Int. Cl.² ........................................ C07D 501/32
[58] Field of Search .............................. 260/243 C

[56] References Cited
UNITED STATES PATENTS

| | | | |
|---|---|---|---|
| 3,796,801 | 3/1974 | Guarini | 260/243 C |
| 3,855,213 | 12/1974 | Dunn et al. | 260/243 C |
| 3,867,380 | 2/1975 | Dunn et al. | 260/243 C |

*Primary Examiner*—Nicholas S. Rizzo
*Assistant Examiner*—Jose Tovar
*Attorney, Agent, or Firm*—William B. Scanlon; Everet F. Smith

[57] ABSTRACT

7-(4-Hydroxyphenylglycylamido)-3-(1-methyl-1H-tetrazolyl-5-thiomethyl)-3-cephem-4-carboxylic acid, 7-(4-hydroxyphenylglycylamido)-3-(5-methyl-1,3,4-thiadiazolyl-2-thiomethyl)-3-cephem-4-carboxylic acid, the corresponding 3-hydroxy isomers and the pharmaceutically acceptable, non-toxic salts thereof are orally effective antibiotics exhibiting high blood levels.

3 Claims, No Drawings

HYDROXY SUBSTITUTED PHENYLGLYCYLAMIDO-3-HETEROCYCLIC THIOMETHYL CEPHALOSPORINS

BACKGROUND OF THE INVENTION

This invention relates to antibiotics of the cephalosporin class. In particular, it relates to 3,7-disubstituted cephalosporins wherein the 3-position substituent is either the 1-methyl-1H-tetrazolyl-5-thiomethyl group or the 5-methyl-1,3,4-thiadiazolyl-2-thiomethyl group and the 7-position substituent is the D-4-(or -3-)hydroxyphenylglycylamido group.

In U.S. Pat. No. 3,641,021, issued Feb. 8, 1972, to Ryan, certain 7-mandelamido and 7-phenylglycylamido substituted cephalosporins having the above-described heterocyclic thiomethyl substituents are described as possessing stability to liver enzymes and cephalosporinase enzymes. Included among a number of substituents which may be present on the phenyl ring of the mandelamido or phenylglycylamido side chain is the hydroxy group. Ryan does not describe with any particularity any specific hydroxyphenylglycylamido substituted cephalosporin in contrast with the description provided for the phenylglycylamido and mandelamido 7-position side chains wherein the phenyl rings are unsubstituted.

SUMMARY

7-[4-(and 3-)Hydroxyphenylglycylamido]-3-(1-methyl-1H-tetrazolyl-5-thiomethyl)-3-cephem-4-carboxylic acid and 7-[4-(and 3-)hydroxyphenylglycylamido]-3-(5-methyl-1,3,4-thiadiazolyl-2-thiomethyl)-3-cephem-4-carboxylic acid, the pharmaceutically acceptable non-toxic salts and certain biologically active esters hereof have been found to possess outstanding antibiotic activity against a broad spectrum of pathogenic microorganisms. The antibiotics in the zwitterionic, salt, or ester form are effective when administered orally and are highly absorbed as reflected by high blood levels obtained following administration. In addition, the blood levels are maintained over a longer period of time following the administration of a single dose than are the blood levels obtained with the unsubstituted phenylglycylamido cephalosporins described by U.S. Pat. No. 3,641,021. In this respect, the cephalosporin antibiotics of this invention are superior to those described in the aforementioned patent.

DETAILED DESCRIPTION

The cephalosporin antibiotics of this invention are represented by the following formula:

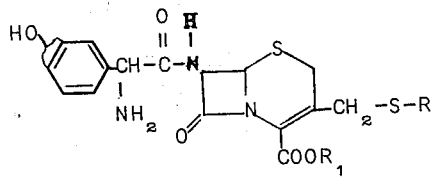

wherein R is the 1-methyl-1H-tetrazolyl group of the formula

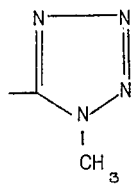

or the 5-methyl-1,3,4-thiadiazolyl group of the formula

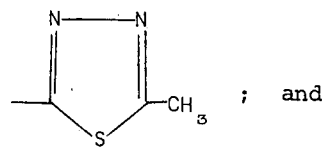 ; and $R_1$ is hydrogen, or a biologically active ester forming group selected from the group consisting of an acyloxymethyl group of the formula

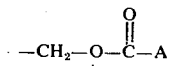

wherein A is $C_1$-$C_4$ alkyl or phenyl; phthalidyl or indanyl; and the pharmaceutically acceptable non-toxic salts thereof.

The cephalosporins of the above formula are prepared but acylating the 7-amino nucleus compounds represented by the formula

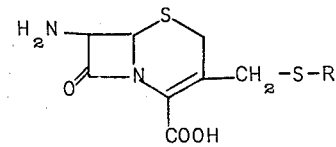

with an amino-protected derivative of 3-, or 4-hydroxyphenylglycine represented by the formula

In the above formulae, R has the same meanings as described previously and P represents an amino-protecting group such as one forming a urethane with the amino group, for example, trichloroethoxycarbonyl, t-butyloxycarbonyl, benzyloxycarbonyl, p-nitrobenzyloxycarbonyl and the like. Or P can be an enamine-protecting group such as that formed with methyl or ethyl acetoacetate or other suitable amino protecting group which can be readily removed following the acylation of the nucleus compound. The amino protecting group is attached to the amino group of the 3-, or 4-hydroxyphenylglycine for the purpose of preventing undesirable acylation with the carboxyl group of another phenylglycine molecule during the desired acylation of the 7-aminocephalosporin nucleus with D-3-, or 4-hydroxyphenylglycine.

The 7-amino-3-(1-methyl-1H-tetrazole-5-ylthiomethyl)-3-cephem-4-carboxylic acid of the formula

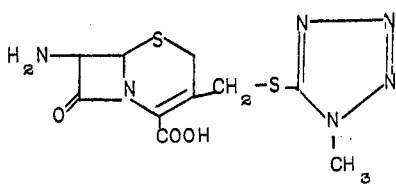

and 7-amino-3-(5-methyl-1,3,4-thiadiazole-2-ylthiomethyl)-3-cephem-4-carboxylic acid of the formula

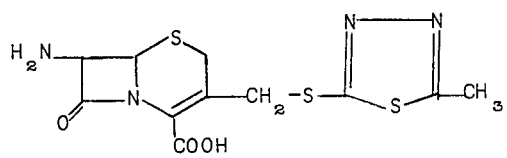

are prepared by methods well known in this art, for example, as described in U.S. Pat. Nos. 3,641,021 and 3,516,997. In general, 7-aminocephalosporanic acid is reacted with 1-methyl-1H-tetrazole-5-thiol or with 5-methyl-1,3,4-thiadiazole-2-thiol in an inert solvent at a basic pH, for example, in aqueous acetone in the presence of sodium carbonate or bicarbonate to effect the nucleophilic displacement of the acetoxy group of 7-ACA to provide the 3-heterocyclic thiomethyl substituted nucleus compounds depicted above.

The acylation of the above 7-amino nucleus compounds can be carried out by following the general acylation procedures well known in the art. For example, the amino protected hydroxyphenylglycine can be reacted with the 7-amino nucleus compound as the free acid in the presence of a condensing agent such as dicyclohexylcarbodiimide or it can be reacted with the nucleus in the form of an active derivative of the carboxylic acid function such as an acid halide, acid azide, or as a mixed anhydride.

In preparing the antibiotics of this invention, certain procedures are preferred in that best yields of higher quality products are obtained with their use. The preferred amino-protecting group, P, useful in the acylation of the nucleus is the enamine protecting group formed with methyl acetoacetate. The preferred acylation method employs the enamine-protected D-3- or 4-hydroxyphenylglycine as the mixed anhydride formed with methyl chloroformate. In an example of the preferred manner of synthesis, D-4-hydroxyphenylglycine is reacted under anhydrous conditions in methanol with sodium hydroxide to form an insoluble suspension of the sodium salt. Methyl acetoacetate is added to the suspension and the mixture is heated at the reflux temperature to provide the enamine-protected 4-hydroxyphenylglycine sodium salt represented by formula A.

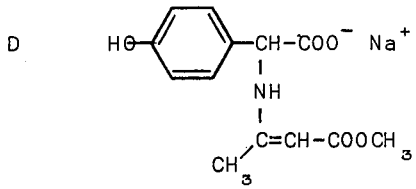

Alternatively, the sodium salt of 4-hydroxyphenylglycine can be solubilized via silylation of the 4-hydroxy group with a silylating agent such as mono- or bis-trimethylsilylacetamide prior to the reaction with methyl acetoacetate.

The enamine salt of 4-hydroxyphenylglycine is converted in dry acetonitrile to the soluble silylated derivative with trimethylsilylacetamide and is then converted to the mixed anhydride formed with methyl chloroformate. The formation of the mixed anhydride is carried out under dry conditions at temperatures below about −10° to −15°C. and preferably about −30° to −35°C. in an inert solvent, e.g., acetonitrile. A catalytic amount of a tertiary amine is used to catalyze the mixed anhydride formation. Diethylaniline, triethylamine and other tertiary amines can be used. Dimethylbenzylamine is a preferred catalyst.

The enamine-protected mixed anhydride derivative represented by formula B below is kept cold and used without isolation to acylate the 7-amino nucleus compound.

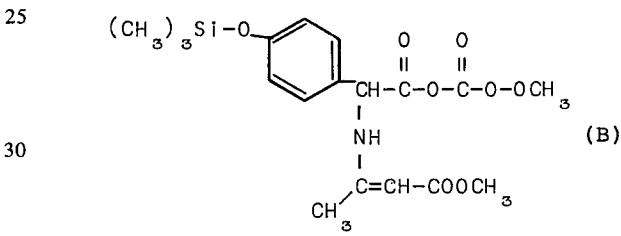

For example, 7-amino-3-(5-methyl-1,3,4-thiadiazole-2-ylthiomethyl)-3-cephem-4-carboxylic acid is suspended in dry acetonitrile and is converted to the soluble silylated derivative with MSA. The acylation is carried out by mixing the two solutions together under nitrogen at about 0°C. or below. The intermediate, enamine-protected acylation product, 7β-[2-[2-(2-methoxycarbonyl-1-methylvinyl)amino]-2-(4-hydroxyphenyl)acetamido]-3-(5-methyl-1,3,4-thiadiazol-2-ylthiomethyl)-3-cephem-4-carboxylic acid is isolated as the crystalline sodium salt by treating the filtered acylation mixture with a solution of an equivalent amount of sodium 2-ethylhexanoate in methanol.

The enamine-protecting group is removed from the intermediate acylation product and the free acid of the antibiotic compound obtained in the zwitterionic form by acidification of the salt of the intermediate. The acidification is carried out in a mixture of water and a water-miscible organic solvent, e.g., acetonitrile and water, with a mineral acid such as sulfuric acid, hydrochloric acid, or nitric acid. Nitric acid is preferred. The intermediate sodium salt is dissolved in the aqueous solvent mixture and the pH of the solution is adjusted to the isoelectric point to precipitate the zwitterionic form of the antibiotic product. The isoelectric point for the zwitterionic compounds of this invention occurs at about pH 4.5.

The above-described acylation and deblocking reactions used in the overall synthesis are illustrated in the following reaction scheme:

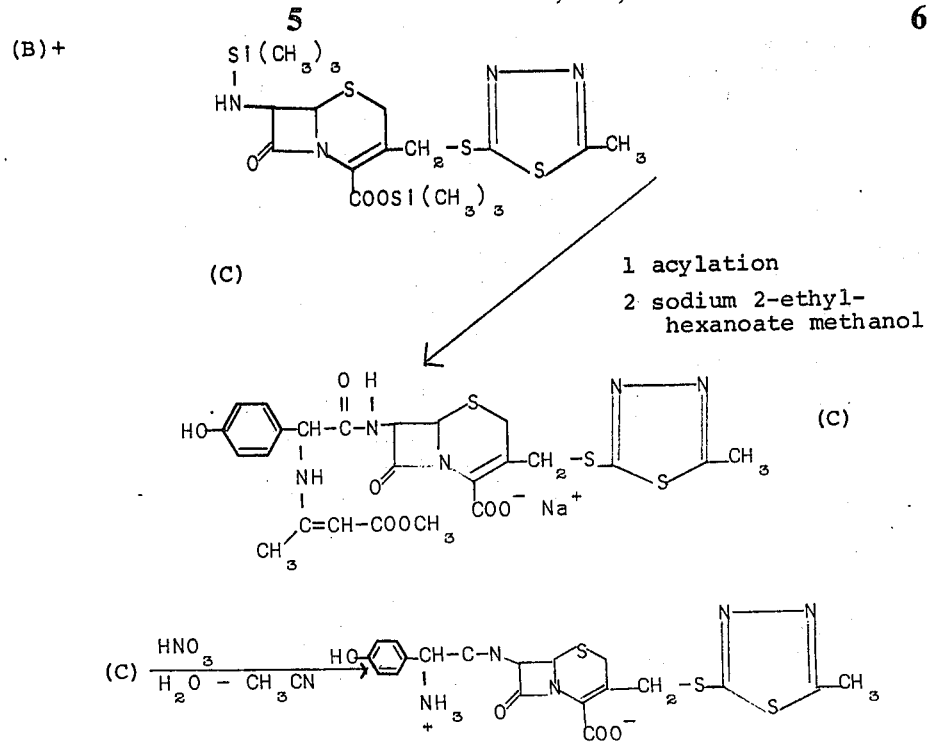

By following the acylation, deblocking, and acidification methods described above, the crystalline zwitterionic form of 7β-(4-hydroxyphenylglycylamido)-3-(1-methyl-1H-tetrazole-5-ylthiomethyl)-3-cephem-4-carboxylic acid, 7β-(3-hydroxyphenylglycylamido)-3-(1-methyl-1H-tetrazole-5-ylthiomethyl)-3-cephem-4-carboxylic acid and 7β-(3-hydroxyphenylglycylamido)-3(5-methyl-1,3,4-thiadiazole-2-ylthiomethyl-3-cephem-4-carboxylic acid are prepared.

The antibiotics of formula I wherein R is hydrogen can be converted to pharmaceutically acceptable salts with inorganic bases and amines. The sodium and potassium salts of the antibiotics can be prepared with sodium and potassium carbonate. Lithium carbonate forms the lithium salt when reacted with the acid form of the antibiotic. Salts formed with nontoxic, pharmaceutically acceptable amines are, for example, the dimethylammonium salt formed with dimethylamine, the dicyclohexylamine salt formed with dicyclohexylamine, the diethanolamine salt formed with diethanolamine, the salt formed with tris-(hydroxymethyl)aminomethane (tris-buffer) and like amine salts.

The compounds of formula I wherein R is an indanyl group of the formula

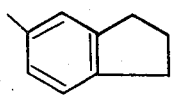

the indanyl esters, are prepared by reacting 5-indanol in an inert solvent such as dioxane or tetrahydrofuran with the free acid form of the cephalosporin of formula I wherein R is hydrogen, in the presence of a condensing agent such as a diimide, for example, dicyclohexylcarbodiimide. The reaction is carried out in an inert solvent at about 20°–35°C. for about 6 to 8 hours. The indanyl ester is recovered by first diluting the reaction mixture with water and filtering to remove the insoluble dicyclohexylurea side product. The ester is then extracted from the filtrate.

The phthalidyl esters of formula I wherein R is a phthalidyl group of the formula

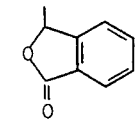

are obtained by reacting bromophthalide of the formula

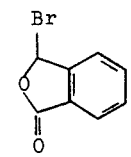

with a salt of a cephalosporin acid of formula I. The esterification can be carried out in dimethylformamide, dimethylacetamide, tetrahydrofuran, or dioxane by heating a mixture of equimolar amounts of the cephalosporin salt with bromophthalide. The sodium or potassium salt of the cephalosporin acid can be used in the reaction.

The cephalosporin antibiotics of the formula I wherein R is hydrogen are converted to the acyloxymethyl esters, wherein R is represented by the group

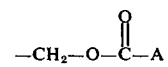

by reacting an alkali metal salt of the cephalosporin carboxylic acid, for example, the lithium, sodium, or potassium salt, with an acyloxymethyl halide of the formula

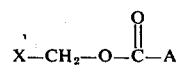

wherein X is chloro or bromo and A has the same meanings as previously defined. Acyloxymethyl halides which can be employed include chloromethyl acetate, bromomethyl acetate, bromomethyl propionate, chloromethyl pivaloate, and benzoyloxymethyl chloride.

The preferred forms of the cephalosporin antibiotics of this invention are the free acids, the pharmaceutically acceptable salts thereof, and the zwitterionic forms of the free acid form.

The preferred antibiotics are the 4-hydroxy substituted cephalosporins.

An especially preferred antibiotic of this invention is 7β-(D-4-hydroxyphenylglycylamido)-3-(5-methyl-1,3,4-thiadiazol-2-ylthiomethyl)-3-cephem-4-carboxylic acid.

The cephalosporin compounds of this invention (Formula I, $R_1$=H) are orally effective broad spectrum antibiotics which are useful in controlling infections caused by gram-positive and gram-negative bacteria. In addition to possessing the high activity usually exhibited by cephalosoporins against the gram-positive microorganisms, they also possess a high level of activity against a broad range of gram-negative bacteria. In Table I, below, the antibacterial activity of the compounds of formula I wherein $R_1$ is hydrogen is illustrated. The bacteria are gram-negative bacteria and the activity is presented as minimum inhibitory concentrations in micrograms per milliliter (mcg./ml.). The activity was obtained by the Gradient-plate technique.

tration of these antibiotics in the blood remains high over a long period of time following administration. These antibiotics have low $ED_{50}$ values (Effective Dose) which, because of their high absorption and prolonged duration of blood levels, can be maintained for extensive periods.

In the tables which follow, a comparison of the $ED_{50}$ values, peak blood levels, and the concentration of antibiotic in the blood measured with time, for antibiotics of this invention (formula I, $R_1$=H) and the 7-phenylglycylamido cephalosporins described in U.S. Pat. No. 3,641,021 is presented.

In Table II, the respective effective doses ($ED_{50}$) for these antibiotics is presented. The data were obtained in mice infected with the indicated microorganism following oral administration of the antibiotics at 1 and 5 hours post infection.

In the tables, R and $R_2$ refer to the test compound represented by the formula

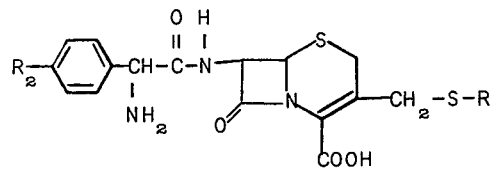

Table II

| | Test Cephalosporin[2] | | Oral Therapy of Experimental Infections in Mice Effective Dose ($ED_{50}$)[1] | | | |
|---|---|---|---|---|---|---|
| No. | R | $R_2$ | Streptococcus pyogenes C203 | Diplococcus pneumoniae Park I | Proteus mirabilis PR6 | Escherichia coli EC14 |
| 1 | Hydroxy | Tet | 0.18 | <1.1 | <4.5 | 3.7 |
| 2 | Hydrogen | Tet | 4.05 | ND[3] | ND | 8.4 |
| 3 | Hydroxy | Thiad | 0.08 | <1.1 | <4.5 | 2.1 |
| 4 | Hydrogen | Thiad | 1.15 | 5.2 | 20.7 | 6.9 |

[1]mg./kg. × 2 oral doses (gavage) at 1 and 5 hours post infection.
[2]Tet represents the 1-methyl-1H-tetrazol-5-yl-radical. Thiad represents the 5-methyl-1,3,4-thiazole-2-yl-radical.
[3]Not determined.

Table 1

Antibacterial Activity vs. Gram-Negative Bacteria

| Test Bacteria | Minimum Inhibitory Concentration (mcg./ml.) Test Compound[1] | | |
|---|---|---|---|
| | A | B | C |
| Shigella sp. | 2.0 | 0.8 | 0.8 |
| Escherichia coli | 2.5 | 1.0 | 0.9 |
| Klebsiella pneumoniae | 1.0 | 1.0 | 0.6 |
| Aerobacter aerogenes | 1.0 | 0.7 | 0.9 |
| Salmonella heidelberg | 1.0 | 0.6 | 0.8 |
| Pseudomonas aeruginosa | >200 | >200 | 120 |
| Serratia marcescens | 47.5 | 12.5 | 5.0 |

[1]A=7β-(D-4-hydroxyphenylglycylamido)-3-(5-methyl-1,3,4-thiadiazole-2-ylthiomethyl)-3-cephem-4-carboxylic acid. B=7β-(D-4-hydroxyphenylglycylamido)-3-(1-methyl-1H-tetrazole-5-ylthiomethyl)-3-cephem-4-carboxylic acid. C=7β-(D-4-hydroxyphenylglycylamido)-3-(1-methyl-1H-tetrazole-5-ylthiomethyl)-3-cephem-4-carboxylic acid.

The antibiotics of this invention in the free acid form also inhibit the growth of clinical isolates of the gram-negative bacteria, Enterobacter, for example, E. aerogenes and E. cloacae; Proteus, e.g., P. morganii, P. rettgeri, P. vulgaris, and P. mirabilis; Klebsiella, e.g., K. pneumoniae, and other species.

As previously mentioned, the hydroxyphenylglycylamido substituted cephalosporins described herein exhibit high blood levels when administered orally. Further, and of greater significance, the concenwherein R is 5-methyl-1,3,4-thiadiazol-2-yl- or 1-methyl-1H-tetrazol-5-yl- and $R_2$ is hydrogen or hydroxy. The compounds of this invention are represented when $R_2$ is hydroxy and those described by Ryan in U.S. Pat. No. 3,641,021 are represented when $R_2$ is hydrogen.

As illustrated by the $ED_{50}$ data in Table II obtained with compound Nos. 1 and 3, the cephalosporin antibiotics of this invention exhibit effective doses greatly superior to those exhibited by the antibiotics of the prior art (compound Nos. 2 and 4). For example, in the treatment of S. pyogenes infections in mice compound No. 3, a preferred compound of this invention, exhibits an $ED_{50}$ value approximately 14 times lower than that exhibited by compound No. 4 (1.15/0.08) and approximately 50 times lower than that exhibited by compound No. 2 (4.05/0.08).

In the following Table III, the concentration of the antibiotic in the blood of mice at time intervals following a single oral dose of 20 mg./kg. is presented. The determinations were carried out in groups of 3 or 4 mice as indicated in the table and the results averaged. The average concentrations are reported in the table. At the indicated time intervals post administration, blood samples were withdrawn at the orbital sinus from each mouse in the test group and assayed for the concentration of antibiotic. The whole blood samples were assayed by the standard agar disc-plate method employing *Sarcina lutea* as the test microorganism.

Table III

| Time (min.) Post Administration[a] | Duration of Antibiotic Blood Levels Average Concentration (mcg./ml.) Cephalosporin Antibiotic[b] | | | |
|---|---|---|---|---|
| | 1[c] | 2[d] | 3[c] | 4[d] |
| 10 | 2.56 | 0.26 | 10.6 | 1.98 |
| 20 | 5.78 | 0.75 | 13.2 | 3.38 |
| 30 | 8.55 | 1.17 | 13.9 | 3.99 |
| 60 | 8.88 | 0.89 | 14.3 | 2.34 |
| 90 | 6.94 | 1.09 | 9.8 | 1.61 |
| 120 | 5.36 | ND[e] | 5.2 | ND[e] |

[a]20 mg. orally administered to each mouse by gavage.
[b]Cephalosporin compound numbers refer to the same compounds so numbered in Table II.
[c]The value is the average of a group of 4 mice.
[d]The value is the average of a group of 3 mice.
[e]Not determined.

The data shown in Table II demonstrate that the 3-, and 4-hydroxyphenylglycylamido cephalosporins of this invention exhibit blood levels superior to those exhibited by the non-hydroxylated phenylglycylamido cephalosporins of the prior art (compound Nos. 2 and 4). As shown in Table III, the 4-hydroxyphenylglycylamido cephalosporins of this invention (compound Nos. 1 and 3) the tetrazole (compound No. 1) and thiadiazole (compound No. 3) 3-substituted compounds give peak blood levels of about 8.9 mcg./ml. and about 14.3 mcg./ml., respectively. In contrast, the non-hydroxylated phenylglycylamido cephalosporins having the tetrazole (compound No. 2) and thiadiazole (compound No. 4) substituent in the 3-position have much lower peak blood levels of about 1.2 mcg./ml. and about 4.0 mcg./ml., respectively.

The cephalosporin antibiotics provided by this invention as the free acids and the pharmaceutically acceptable non-toxic salts thereof are highly effective antibiotics which are superior oral therapeutic agents. They can also be administered parenterally, for example, subcutaneously or by the intramuscular route.

The free acid forms of the antibiotics can be converted to pharmaceutically acceptable salt forms with suitable acids and bases. For example, the $C_4$ carboxylic acid function can be neutralized with both organic amines and inorganic bases by methods well known in this art. Suitable inorganic bases include the alkali and alkaline earth metal carbonates, bicarbonates, and hydroxides such as lithium carbonate, sodium carbonate, potassium carbonate, sodium bicarbonate, calcium hydroxide, sodium hydroxide, and the like. Illustrative salts formed with these bases include the lithium, sodium, potassium and calcium salts.

Organic amines such as dicyclohexylamine, diethylamine, benzylamine, dibenzylamine, tris-hydroxymethylaminomethane (tris buffer), monoethanolamine, diethanolamine, and like amines can be used to form suitable salts. Ammonium hydroxide can be employed in the neutralization of the $C_4$ carboxylic acid function to prepare the ammonium salt.

The term "pharmaceutically acceptable salts" also refers to the acid addition salts of the α-amino group in the 7-position side-chain. Acid addition salts formed with mineral acids such as hydrochloric acid, hydrobromic acid, and phosphoric acid can be used. Likewise, acid addition salts formed with organic sulfonic acids such as the lower alkylsulfonic acids, methanesulfonic acid, and ethanesulfonic acid; the aromatic sulfonic acids such as p-toluenesulfonic acid and the naphthalenesulfonic acids can be prepared.

The previously described acyloxymethyl, indanyl, and phthalidyl esters of the cephalosporin antibiotics provided herein are also useful in combatting infections when administered orally to the infected host. Representative "active esters" include the acetoxymethyl, pivaloyloxymethyl, benzoyloxymethyl, indanyl, and phthalidyl esters of both 4-hydroxyphenylglycylamido substituted cephalosporins.

This invention is further illustrated by the following examples.

EXAMPLE 1

To a suspension of 23.9 g. (.143 M) of D-4-hydroxyphenylglycine in 150 ml. of methanol were added 6 g. (ca. 0.145 M) of sodium hydroxide pellets. The mixture was heated at 60°C. with stirring for about 15 minutes during which time the sodium salt of the acid formed a thick slurry. To the slurry were added 20.1 ml. (.186 M) of methyl acetoacetate and the mixture was heated at the reflux temperature of approximately 68°C. for 90 minutes. After about 20 minutes at the reflux temperature, a clear solution was obtained and following 20 additional minutes, the product began to crystallize from the clear solution. With continued heating at the reflux temperature, 300 ml. of acetonitrile were added dropwise over a 15 minute period. Thereafter, the solvent methanol was allowed to distill out of the mixture while another 300 ml. of acetonitrile was added dropwise over approvimately 75 minutes. The reaction mixture was allowed to cool to room temperature with continued stirring. The crystalline product precipitated at room temperature, was filtered and washed with approximately 200 ml. of acetonitrile. The product, the sodium salt of the methyl acetoacetate enamine of D-4-hydroxyphenylglycine, was dried to yield 40 g. of white, crystalline solid (97 percent yield).

To a 1 liter round-bottomed three-necked flask equipped with a mechanical stirrer, a thermometer, and a dry nitrogen purge were added 100 ml. of dry acetonitrile and 16.5 g. (113 mM) of trimethylsilylacetamide (MSA) which was washed in with an additional 50 ml. of dry acetonitrile. To this solution 35.0 g. (113 mM) of the dry sodium salt of the methyl acetoacetate enamine of D-4-hydroxyphenylglycine prepared as described above were added and rinsed in with a further 100 ml. of dry acetonitrile. The mixture was then stirred with warming to approximately 50°C. to form a thick slurry. The slurry was cooled in an acetone dry ice bath to −35°C. and 10 drops of dimethylbenzylamine were added, followed by the addition of 10.7 g. (113 mM) of methylchloroformate. As the methylchloroformate was added, the slurry initially thickened and then thinned considerably as the insoluble sodium salt of the enamine protected 4-hydroxyphenylglycine was converted to the soluble mixed anhydride. During the above addition the temperature of the reaction mixture increased to approximately −30°C. and was cooled following addition to −40°C.

In the meantime, in a separate 300 ml. round-bottomed flask were added 100 ml. of dry acetonitrile, 58.9 g. (450 mM) of trimethylsilylacetamide and 35.9 g. (100 mM) of dry 7-amino-3-(5-methyl-1,3,4-thiadiazole-2-ylthiomethyl)-3-cephem-4-carboxylic acid. Approximately 50 ml. of dry acetonitrile were used to wash the reagents into the flask. The mixture, protected with a drying tube was stirred at room temperature until solution was complete. The solution was then cooled in an acetone-dry ice bath until crystallization was initiated. The cold solution of the silylated nucleus compound was then added under dry nitrogen to the cold solution of the mixed anhydride of the enamine-protected 4-hydroxyphenylglycine compound prepared as described above. During the addition the temperature of the mixture increased to approximately −30°C. and following the addition was cooled again to −40°C. Thereafter the reaction mixture was allowed to warm slowly to 0°C. over a 90-minute period. Hyflo filter aid was added to the reaction mixture which was then filtered through a Hyflo filter pad. The filter was washed with dry acetonitrile and the washings were combined with the filtrate. The filtrate was warmed to room temperature and a solution of 16.6 g. (100 mM) of sodium 2-ethylhexanoate in 50 ml. of methanol was added to the filtrate with stirring. Crystallization of the product, the sodium salt of 7β-[2-(2-methoxycarbonyl-1-methylvinyl-amino)-2-(4-hydroxyphenyl)-acetamido]-3-(5-methyl-1,3,4-thiadiazole-2ylthiomethyl)-3-cephem-4-carboxylic acid, began in a few minutes and the mixture was allowed to stand for 2 hours at room temperature to complete the crystallization. The product was filtered and was washed with acetonitrile and then with anhydrous diethyl ether. The product was dried in a stream of dry nitrogen and finally in vacuo to yield 46.4 g. (75.7 percent yield).

UV (methanol) $\lambda_{max}$ 232 a$_m$ (16,500), $\lambda_{max}$ 283 a$_m$ (33,400)

IR (mull) 1770 cm$^{-1}$ (β-lactam carbonyl), 1675 (amide)

NMR 100 MHz (DMSOd$_6$) 1.76 (3H, s), 2.65 (3H, s), 3.30 (1H, d, J=17 hz), 3.4 (broad), 3.51 (1H, d, J=17 hz), 3.52 (3H, s), 4.35 (1H, d, J=12 hz), 4.45 (1H, s), 4.50 (1H, d, J=12 hz), 4.88 (1H, d, J=5 hz), 5.37 (1H, d, J=8 hz), 5.53 (1H, d/d, J=5, 8 hz), 6.73 (2H, d, J=8.5 hz), 7.16 (2H, d, J=8.5 hz), 9.20 (1H, d, J=8 hz), 9.26 (1H, d, J=8 hz) delta.

To a 200 ml. Erlenmeyer flask containing 70 ml. of a mixture of acetonitrile and water (3:1), (v:v) were added with vigorous stirring, 30.7 g. (50 mM) of the product obtained as described above. An additional 30 ml. of the same solvent mixture was employed to wash the crystalline material into the flask. When solution was obtained, the pH of the solution was approximately 8.8. Concentrated nitric acid was added dropwise to the solution to adjust the pH to approximately pH 7. The solution was warmed to about 50°C. and was seeded with crystalline 7β-(D-4-phenylglycylamido)-3-(5-methyl-1,3,4-thiadiazole-2-yl-thiomethyl)-3-cephem-4-carboxylic acid while nitric acid addition was continued slowly. The pH of the solution was adjusted to pH 4.5 whereupon the product precipitated as the insoluble zwitterionic form. A total of 3.8 ml. of nitric acid were employed in adjusting the pH. The mixture was allowed to cool to room temperature over about 2 hours and was then filtered. The filter cake was washed with 60 ml. of 3:1, v:v, acetonitrile:water in several portions, then with 60 ml. of acetonitrile in several portions and was then dried under nitrogen and finally dried in vacuo. The yield of the product was 50.8 g. (64 percent), 48 percent overall.

UV (methanol) $\lambda_{max}$ 232 a$_m$ (16,270), $\lambda_{max}$ 275 a$_m$ (15,390)

IR (mull) 1790 cm$^{-1}$

100 MHz NMR (DMSOd$_6$ + monodeutero-trifluoroacetic acid) 2.66 (3H, s), 3.50 (1H, d, J=18 hz), 3.67 (1H, d, J=18 hz), 4.18 (1H, d, J=13.5 hz), 4.47 (1H, d, J=13.5 hz), 4.90 (1H, broad), 5.05 (1H, d, J=4.5 hz), 5.76 (1H, d/d, J=4.5, 8.5 hz), 6.78 (2H, d, J=8.5), 7.20 (2H, d, J=8.5), 8.62 (broad), 9.43 (1H, d, J=8.5 hz) delta.

$[\alpha]_D^{25°}$ (4:1 DMSO 1N HCl) −63°

Electrometric titration (6 percent DMF) pK$_a$ 4.4, 7.6 and 12.2. Apparent MW 506, Calc. MW 494.

EXAMPLE 2

By employing the procedures described by Example 1, the mixed anhydride formed with the enamine (methyl acetoacetate) protected 4-hydroxyphenylglycine and methyl chloroformate is employed to acylate the silylated nucleus, 7-amino-3-(1-methyl-1H-tetrazole-5-ylthiomethyl)-3-cephem-4-carboxylic acid, in acetonitrile to form the enamine-protected 7β-(4-hydroxyphenylglycylamido)-3-(1-methyl-1H-tetrazole-5-ylthiomethyl)-3-cephem-4-carboxylic acid. The enamine-protected acylation product is precipitated from the filtered acylation mixture as the insoluble sodium salt formed when a solution of sodium 2-ethylhexanoate is added to the mixture. The sodium salt of the enamine protected acylation product is filtered and washed and is then treated in acetonitrile and water with nitric acid to adjust the pH of the solution to the isoelectric point. The product, 7β-(4-hydroxyphenylglycylamido)-3-(1-methyl-1H-tetrazole-5-ylthiomethyl)-3-cephem-4-carboxylic acid, precipitates in the zwitterionic form and is recovered by filtration.

EXAMPLE 3

To a suspension of 3.29 g. of 7-amino-3-(5-methyl-1,3,4-thiadiazole-2-ylthiomethyl)-3-cephem-4-carboxylic acid in dry tetrahydrofuran was added excess mono-silylacetamide to form a solution of the soluble silylated derivative of the amine nucleus.

In the meantime, to a solution of 2.67 g. of N-(t-butyloxycarbonyl)-3-hydroxyphenylglycine in 200 ml. of dry tetrahydrofuran were added about 6 drops of N,N-dimethylbenzylamine. The solution was cooled to about −22°C. and 1 ml. of triethylamine was then added. To the cold solution were added 1.4 g. of isobutyl chloroformate to form the mixed anhydride of the t-butyloxycarbonyl protected 3-hydroxyphenylglycine. The cold solution of the mixed anhydride was added to the previously prepared cold solution of the silylated nucleus and the mixture was stirred at about −22°C. for 2 hours, and then at 0°C. for one hour. The reaction mixture was filtered and 15 ml. of methanol were added to the filtrate. The methanol treated filtrate was filtered and evaporated under vacuum. An equal volume of a mixture of ethyl acetate and water was added to the residue and the pH was adjusted to pH 2. The reaction product was converted to the sodium salt with aqueous 1N sodium hydroxide, the pH readjusted to ph 2 with 1N hydrochloric acid and the product, as the free cephalsoporin carboxylic acid, was extracted with ethyl acetate. The extract was washed with water, dried, and evaporated under vacuum to yield 1.944 g. of the t-butyloxycarbonyl protected 7β-(D-3-hydroxyphenylglycylamido)-3-(5-methyl-1,3,4-thiadiazole-2-ylthiomethyl)-3-cephem-4-carboxylic acid.

The product was reacted with excess trifluoroacetic acid to remove the t-butyloxycarbonyl protecting group and provide the product.

I claim:
1. The cephalosporin compound of the formula

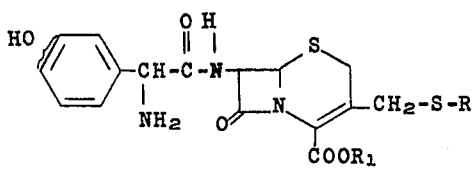

wherein R is the 1-methyl-1H-tetrazol-5-yl group of the formula

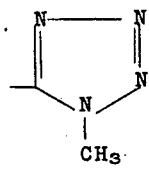

or the 5-methyl-1,3,4-thiadiazol-2-yl group of the formula

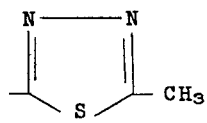

and $R_1$ is selected from the group consisting of 5-indanyl, phthalidyl, and an acyloxymethyl group of the formula

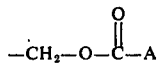

wherein A is $C_1$-$C_4$ alkyl or phenyl.

2. The compound of claim 1 wherein R is

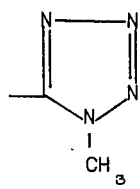

3. The compound of claim 1 wherein R is

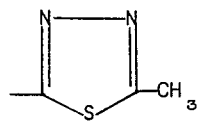

* * * * *